(12) United States Patent
Assa et al.

(10) Patent No.: US 12,714,498 B2
(45) Date of Patent: Aug. 25, 2026

(54) DEVICE AND METHOD USING LASER CORING TO FORM INDEPENDENT LIFTING VECTORS FOR CONTROLLED PULLING ON HUMAN SKIN

(71) Applicant: Acclaro Corporation, Smithfield, RI (US)

(72) Inventors: Shlomo Assa, Lincoln, RI (US); David Friedman, Jerusalem (IL); Yingyuan Fang, Lincoln, RI (US); John Vachon, Lakeville, MA (US)

(73) Assignee: ACCLARO CORPORATION, Smithfield, RI (US)

( * ) Notice: Subject to any disclaimer, the term of this patent is extended or adjusted under 35 U.S.C. 154(b) by 290 days.

(21) Appl. No.: 18/376,069

(22) Filed: Oct. 3, 2023

(65) Prior Publication Data

US 2025/0107848 A1 Apr. 3, 2025

(51) Int. Cl.
*A61B 18/20* (2006.01)
*A61B 18/00* (2006.01)

(52) U.S. Cl.
CPC .... *A61B 18/203* (2013.01); *A61B 2018/0047* (2013.01); *A61B 2018/00577* (2013.01)

(58) Field of Classification Search
CPC .......... A61B 18/203; A61B 2018/0047; A61B 2018/00577
See application file for complete search history.

(56) References Cited

U.S. PATENT DOCUMENTS

2012/0226268 A1* 9/2012 Liu ...................... A61N 5/0613 606/9
2022/0118277 A1 4/2022 Assa et al.
2022/0175449 A1* 6/2022 Assa .................... A61B 18/203
2023/0034882 A1* 2/2023 Masotti ................ A61N 5/0616

OTHER PUBLICATIONS

Walsh et al., Er: YAG Laser Ablation of Tissue: Measurement of Ablation RateS, Lasers in Surgery and Medicine 9:327-337 (1989).
Walsh et al., Er: YAG Laser Ablation of Tissue: Effect of Pulse Duration and Tissue Type on Thermal Damage, Lasers in Surger and Medicine 9:314-326 (1989).

(Continued)

*Primary Examiner* — Niketa Patel
*Assistant Examiner* — Sebastian X Lukjan
(74) *Attorney, Agent, or Firm* — Panitch Schwarze Belisario & Nadel LLP

(57) ABSTRACT

A laser treatment device includes a laser source configured to emit optical energy at a wavelength between about 2,700-3,500 nm, a laser applicator configured to deliver the optical energy to a target area of human tissue, and a controller configured to control the laser source and applicator to form a hole in the human tissue within the target area by delivering laser pulses to a plurality of locations forming a pattern within the target area. Each of the locations partially overlaps with at least one other of the locations. The controller is configured to provide each of the pulses with a fluence above an ablation threshold fluence for the laser wavelength such that a thermal injury percentage for energy delivered by each pulse is between about 5-50%. The thermal injury percentage is determined by dividing the ablation threshold fluence by the fluence of each pulse.

20 Claims, 4 Drawing Sheets

(56) References Cited

OTHER PUBLICATIONS

Lukac et al., Ablation and Thermal Depths in VSP Er:YAG Laser Skin Resurfacing, Journal of the Laser and Health Academy, 17 pages, vol. No. 1; www.laserandhealth.com (2010).
Walsh et al., Pulsed Co2 Laser Tissue Ablation: Effect of Tissue Type and Pulse Duration on Thermal Damage, Lasers in Surger and Medicine 8:108-118 (1988).
Walsh et al., Pusled CO2 Laser Tissue Ablation: Measurement of the Ablation Rate, Lasers in Surger and Medicine 8:264-275 (1988).
Diaci et al., Review Comparison of Er:YAG and Er, YSGG lasers used in dentistry, Journal of the Laser and Health Academy, pp. 1-13, vol. 1, www.laserandhealth.com (2012).

* cited by examiner

DEVICE AND METHOD USING LASER CORING TO FORM INDEPENDENT LIFTING VECTORS FOR CONTROLLED PULLING ON HUMAN SKIN

BACKGROUND

Embodiments described herein relate generally to radiation-based dermatological treatment devices and methods, and more particularly, to a laser-based skin tightening system and method.

Exposure of the skin to environmental factors and gravitational forces, and the effects of the normal aging process can, over time, cause the skin to sag, wrinkle, form lines, or develop other undesirable distortions. Even normal contraction of facial and neck muscles, e.g., by frowning or squinting, can also, over time, form furrows or bands in the face and neck region. These effects are often considered to be generally aesthetically unpleasant such that patients with these cosmetic issues often seek treatment to tighten the skin.

A prevalent treatment is a "facelift," which involves the surgical removal of excess skin for a permanent skin-tightening effect. While this surgery can produce dramatic results, it is also highly invasive and results in a long downtime afterward for healing. The procedure can also be very painful, leave lasting scars in the areas of incisions, and is very expensive. The results can also be unreliable, as stories abound of facelifts gone wrong.

Another type of treatment involves radio frequency (RF) or ultrasound bulk heating. In this procedure, high intensity RF or ultrasonic radiation is applied to the skin to encourage the production of collagen for creating firmer skin. Despite being non-invasive, this procedure is also painful. It also takes a significantly long time (e.g., on the order of 2-3 months) to see results from the process, does not produce consistent results, and requires multiple treatments.

Mechanical micro-coring is another technology that was developed to improve skin tightening procedures. The system uses a plurality of punch needles arranged in a pattern that remove small columns (e.g., ~0.5 mm diameter) of skin that can be down to the hypodermis, leaving behind a number of small holes in a grid formation across the treatment area. As the patient heals, the holes close and the skin tightens. However, it can take three or more treatments to see results, which is problematic since the procedure is painful, may cause excessive bleeding, and significantly raises the cost. The procedure is also limited because it can only be performed in the middle and lower areas of the face and is only effective for certain skin types (e.g., only for types I-IV on the Fitzpatrick scale).

Lifting procedures using lasers have also been used. Skin tightening using a $CO_2$ pulsed laser treatment was developed several decades ago. The technique temporarily improves sagging of the skin for a period of several years, but is incredibly painful, requires long patient downtime, and is very risky for side effects, especially to patients with darker skin. More recently, fractionated laser treatments have been used, but the results can be improved upon.

It is desirable to provide a laser treatment for skin tightening that can be used on nearly all areas of the face and neck, provides faster results, decreases treatment time, lowers pain and downtime after the procedure, reduces bleeding, minimizes the need for sterilization, and is safe for all skin types.

BRIEF SUMMARY

Briefly stated, one embodiment comprises a laser treatment device including a laser source configured to emit optical energy at a laser wavelength between about 2,700 nm and about 3,500 nm, a laser applicator configured to receive the optical energy emitted by the laser source and deliver the received optical energy to a target area of human tissue, and a controller configured to control the laser source and laser applicator to form a hole in the human tissue within the target area by delivering a plurality of laser pulses to a plurality of locations forming a pattern within the target area. Each of the plurality of locations in the pattern partially overlaps with at least one other of the plurality of locations in the pattern. The controller is configured to provide each of the plurality of pulses with a fluence above an ablation threshold fluence for the laser wavelength such that a thermal injury percentage for energy delivered by each pulse is between about 5% and about 50%. The thermal injury percentage is determined by dividing the ablation threshold fluence for the laser wavelength by the fluence of each pulse.

In one aspect, the controller is further configured to control the laser source and laser applicator to form a plurality of holes, spaced apart from one another, within the target area. IN a further aspect, the controller is configured to control the laser source and laser applicator to space the plurality of holes apart from one another by a distance of between about 1.000 mm and 4.000 mm in the target area. In a still further aspect, the controller is configured to receive a selection from a user for the distance between the plurality of holes. In a yet further aspect, the controller is configured to one of (i) store a predetermined pattern for arranging the plurality of holes in the target area, or (2) receive a selection from a user of a pattern for arranging the plurality of holes in the target area.

In another aspect, the thermal injury percentage for energy delivered by each pulse is between about 5% and about 35%. In a further aspect, the thermal injury percentage for energy delivered by each pulse is between about 15% and about 25%.

In yet another aspect, the controller is configured to control the laser source and the laser applicator such that at least a portion of the plurality of locations together form a ring. In a further aspect, the controller is configured to control the laser source and the laser applicator such that one of the plurality of locations is located at a center of the ring.

In still another aspect, the controller is configured to continue delivering laser pulses to the target area in the pattern until a set depth of the hole is obtained. In a further aspect, the set depth of the hole is between about 0.5 mm and about 4.0 mm.

In yet another aspect, the laser treatment device further includes a user interface in communication with the controller, wherein the controller is configured to receive, via the user interface, a user selection of one or more of a hole pattern for arranging a plurality of holes to be formed by the laser treatment device, a size of the hole pattern, spacing of the plurality of holes within the hole pattern, or a hole depth.

In still another aspect, the controller is configured to form the hole having a diameter of between about 250 microns and about 400 microns.

In yet another aspect, the controller is configured to set the fluence for each pulse such that an ablation depth of each pulse is between about 25 microns and about 50 microns.

Another embodiment comprises a method of forming a hole in a target area of human tissue using a laser treatment device having a laser source configured to emit optical energy at a laser wavelength between about 2,700 nm and about 3,500 nm, a laser applicator configured to receive the optical energy emitted by the laser source and deliver the received optical energy to the target area, and a controller.

The method includes (a) delivering, by the laser source and the laser applicator, a laser pulse having a set fluence to the target area, (b) changing, by the controller, location in the target area and delivering, by the laser source and the laser applicator, a laser pulse having the set fluence, (c) repeating step (b) to form a pattern including a plurality of locations, each of which partially overlaps with at least one other of the plurality of locations in the pattern. The set fluence for each of the laser pulses is above an ablation threshold fluence for the laser wavelength such that a thermal injury percentage for energy delivered by each pulse is between about 5% and about 50%. The thermal injury percentage is determined by dividing the ablation threshold fluence for the laser wavelength by the fluence of each pulse.

In one aspect, the thermal injury percentage for energy delivered by each pulse is between about 5% and about 35%. In a further aspect, the thermal injury percentage for energy delivered by each pulse is between about 15% and about 25%.

In another aspect, the method further includes repeating delivery of laser pulses in the pattern until a set depth of the hole is obtained. In a further aspect, the set depth of the hole is between about 0.5 mm and about 4.0 mm.

Another embodiment comprises a method of treating human tissue. The method includes forming a plurality of holes in a target area according to the methods described above.

BRIEF DESCRIPTION OF THE SEVERAL VIEWS OF THE DRAWINGS

The following detailed description of preferred embodiments will be better understood when read in conjunction with the appended drawings. For the purpose of illustration, there are shown in the drawings embodiments which are presently preferred. It should be understood, however, that the invention is not limited to the precise arrangements and instrumentalities shown.

In the drawings.

DETAILED DESCRIPTION

Figure 1:
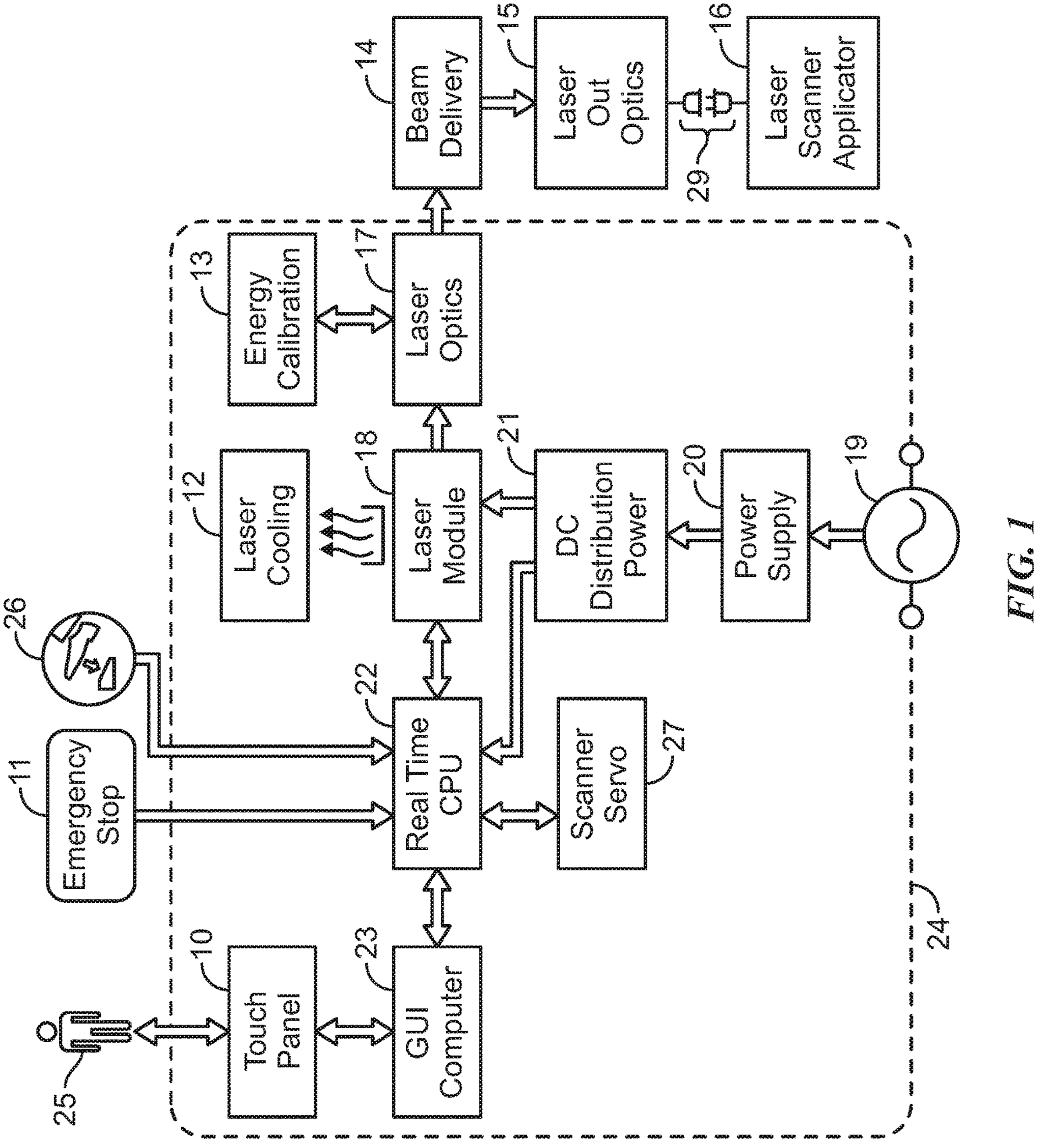
FIG. 1 is a schematic block diagram of a treatment device in accordance with an example embodiment of the present invention.

Certain terminology is used in the following description for convenience only and is not limiting. The words “right”, “left”, “lower”, and “upper” designate directions in the drawings to which reference is made. The words “inwardly” and “outwardly” refer to directions toward and away from, respectively, the geometric center of the device and designated parts thereof. The terminology includes the above-listed words, derivatives thereof, and words of similar import. Additionally, the words “a” and “an”, as used in the claims and in the corresponding portions of the specification, mean “at least one.”

It should also be understood that the terms “about,” “approximately,” “generally,” “substantially” and like terms, used herein when referring to a dimension or characteristic of a component, indicate that the described dimension/characteristic is not a strict boundary or parameter and does not exclude minor variations therefrom that are functionally similar. Such references that include a numerical parameter would include variations that, using mathematical and industrial principles accepted in the art (e.g., rounding, measurement or other systematic errors, manufacturing tolerances, etc.), would not vary the least significant digit.

Referring to FIG. 1, there is shown an example treatment device 24. The treatment device 24 may include a radiation source 18, such as a laser module or the like, configured to generate an energy beam. For example, the radiation device 18 may be a mid-IR fiber laser operating at a wavelength of 2,910 nm, an Er:YAG laser operating at a wavelength of 2,940 nm, an Er:YSGG laser operating at a wavelength of 2,780 nm, or the like, with preferred laser wavelengths being between about 2,700 nm and about 3,500 nm. The device 24 may be powered by a power supply 20, which may be a direct current (DC) medical power supply that may be capable of accepting one or more of a wide range of alternating current (AC) inputs (e.g., mains supply 19 or the like) that are commonly used, such as 110V at 60 Hz, 240 V at 50 Hz, or the like. The power supply 20 may rectify and condition the input AC voltage to an output such as 24 VDC, although other output voltages may be used as well. A power distribution circuit 21 may be provided for receiving power from the power supply 20 for distribution to various components, such as but not limited to, the radiation source 18, throughout the treatment device 24.

The treatment device 24 may include a controller 22, which may be a central processing unit (CPU), a microcontroller unit (MCU), a microprocessor, an application specific controller (ASIC), a programmable logic array (PLA), combinations thereof, or the like. The controller 22 may include or be coupled to a memory (not shown) that may store code or software for carrying out processes described herein and/or carrying out other operations of the treatment device 24 and may store any captured data for later transfer to remote or external devices. It should be further appreciated that although controller 22 is referred to in this example as a single component, the controller 22 may include a plurality of individual devices, with control functions divided among the individual devices. The controller 22 may be wired or wirelessly connected to components of the treatment device 24 necessary for carrying out the operations and processes described herein.

The controller 22 may be connected to a GUI computer 23 or other type of user input device configured to receive and provide to the controller 22 commands related to settings for the treatment device 24. For example, the GUI computer 23 may have a touch panel 10 through which a user 25 may interact to make selections that the GUI computer 23 will then communicate to the controller 22 for selection of appropriate operational programs and settings.

During operation, the radiation source 18 may generate excess heat that may be required to be dissipated to the surrounding environment in order to keep the treatment device 24 within safe operating temperatures. For this purpose, a cooling device 12 may be provided that will extract heat from the radiation source 18 and dissipate the heat to the surrounding environment using a cooling fan (not shown).

The radiation source 18 may emit radiation into a laser optics module 17. The laser optics module 17 may include a series of lenses, mirrors, other optical elements, combinations thereof, or the like, for collimating a beam of radiation for emission. In a preferred embodiment, the beam may have a diameter of about 170 microns, although other diameters may be used as well, based on the treatment conditions. Since the beam is invisible, the laser optics module 17 or other portion of the treatment device 24 may combine the beam with a visible laser (e.g., a 630-650 nm red laser or the like) to allow the user 25 to see the location and movement of the beam.

In some embodiments, the laser optics module 17 may be connected to an energy calibration device 13. The energy calibration device 13 may include, for example, an InAsSb photovoltaic detector optimized to measure laser radiation in the wavelength range of the radiation device (e.g., 2,940 nm or the like), as well as a real time servo controller. The energy calibration device 13 may be configured to read a sample of the main laser beam in real time to control the energy per pulse in such a manner that when the energy selected by the operator 25 or preset in the system has been delivered, the energy calibration detector 13 may send a signal to the controller 22 to cut the laser pulse. The energy calibration detector 13 may be configured to measure a sample of the laser energy and monitor, in a closed loop, the selected or preset energy.

The radiation energy may be directed to a beam delivery device 14, such as a fiber optics device, an arm of rotating mirrors, or the like. The beam delivery device 14 may further direct the radiation energy to a final energy conditioning device, such as laser output optics 15. For example, the laser output optics 15 may be another collection of lenses, mirrors, other optical elements, combinations thereof, or the like, to collimate the laser beam to a diameter of about 170 microns. In other embodiments, the laser output optics 15 may be a protective and replaceable window to prevent dust and contamination from affecting the operating reliability of the radiation source 18. Combinations thereof may be used as well, such as a combination of collimating optics and a protective window, or the like.

In some embodiments, the laser output optics 15 may include a quick disconnect connection 29 to a laser applicator 16, which may be replaceable to achieve different clinical effects. In other embodiments, a single laser applicator 16 may be installed more permanently to the treatment device 24. An example laser applicator is disclosed in U.S. Patent Application Publication No. 2022/0118277, the contents of which are incorporated by reference herein. The treatment device 24 may further include a scanner servo controller 27 that is configured to drive X and Y scanner motors (not shown), which may be located in the laser applicator 16 or elsewhere on the treatment device 24. The scanner servo controller 27 may operate under the control of the controller 22 to move the laser spot according to selected or predetermined programming.

An operator 25 may use a footswitch device 26 to control energy emission to be delivered according to the settings selected or entered through the GUI computer 23 or other type of user input device. For example, the operator 25 may depress the footswitch device 26 to start and/or stop laser operation. Although a footswitch device 26 is shown for this purpose, other mechanisms for controlling laser operation, including other types of buttons, switches, panels, combinations thereof, or the like, may be used as well. In case of emergency, the treatment device 24 may include an emergency stop switch 11.

Figure 2:
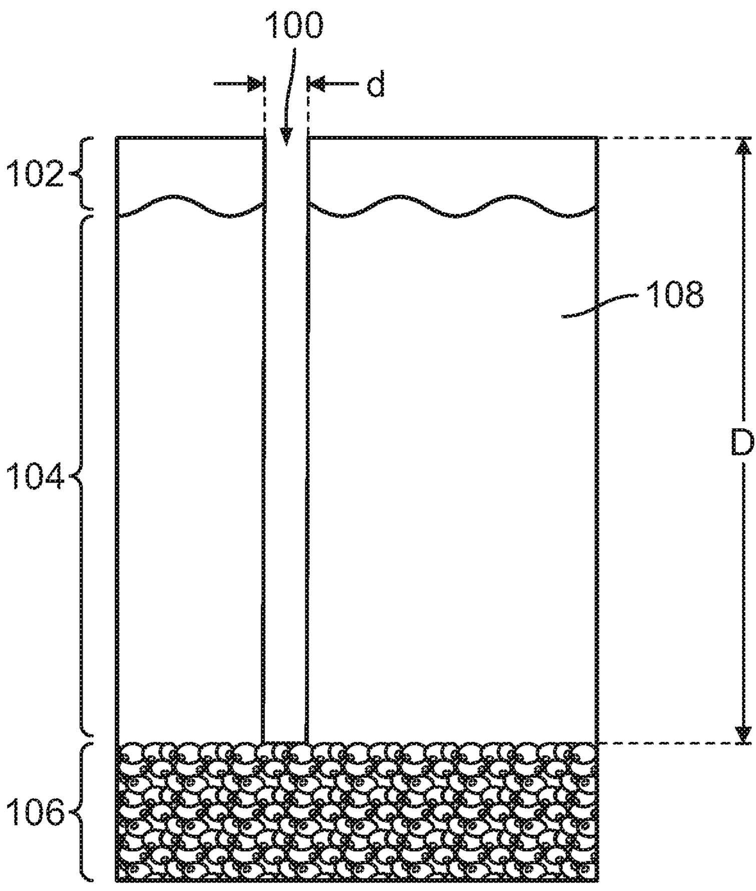
FIG. 2 is a schematic diagram of a hole formed in the skin using a laser coring operation in accordance with an example embodiments of the present invention.

An example laser coring operation, which may be implemented using the treatment device 24 described above or a like radiation treatment device, will now be described. FIG. 2 shows an example hole 100 which may be formed using an example of the laser coring operation. The hole 100 may be formed through the epidermis 102 and into the dermis layer 104 of the skin 108. The hole 100 may extend at least partially through the epidermis 102 and may, in some instances, extend partially into the hypodermis 106, although it is preferred that a bottom of the hole 100 coincides with a top of the hypodermis layer 106. The hole 100 may have a depth D of approximately 1.0 mm, although other depths may be used as well depending on the patient, desired effects, laser capabilities, and the like. Preferably, the depth may be between about 0.5 mm to about 4.0 mm. The hole 100 may also have a cross-sectional diameter d of about 250 microns to about 400 microns, more particularly between about 360 microns to about 400 microns, although other diameters or widths may be used as well, again depending on the patient, desired effects, laser capabilities, and the like.

The laser coring operation described herein does not form the hole 100 using a single laser pulse, as in traditional operations. The overall fluence to drill a 1.0 mm deep, 380 micron diameter hole with a single pulse from a mid-IR or Er:YAG laser is about 250 J/cm$^2$. Given that the ablation threshold is typically about 2 J/cm$^2$, approximately 1% of the delivered energy results in thermal injury (obtained from dividing the ablation threshold fluence for the laser wavelength by the pulse fluence=2/250), with the rest directed to ablation. Forming holes 100 in this fashion is very painful, and, as will be explained in further detail below, does not provide the same type of clinical effect. Using a $CO_2$ laser, which is much less efficient at its 10,640 nm wavelength, a fluence of 750 J/cm$^2$ is required to ablate the same size hole. In addition, approximately 60% of the delivered energy goes to thermal injury while the other 40% is ablative, based on the lower absorption rate. The thermal injury size is too large to create the effect attained using the treatment device described herein, causing substantial downtime and a high risk of complications, such as lasting redness and Post-Inflammatory Hyperpigmentation (PIH).

Figure 3:
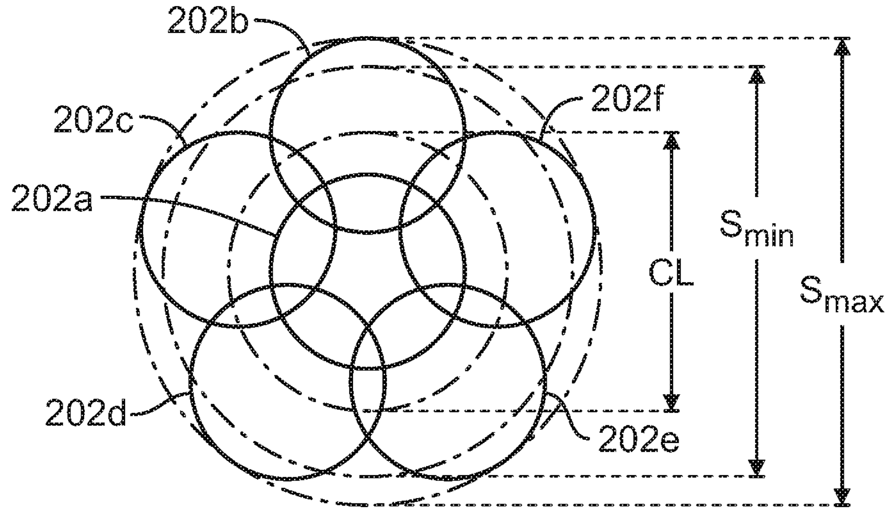
FIG. 3 is a schematic diagram showing an example relative placement of individual pulses in a layer during a laser coring operation in accordance with an example embodiment of the present invention.
Figure 4:
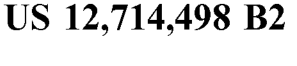
FIG. 4 is a schematic diagram illustrating an example motion of a centerline of laser pulses relative to depth during a laser coring operation in accordance with an example embodiment of the present invention.
Figure 4:
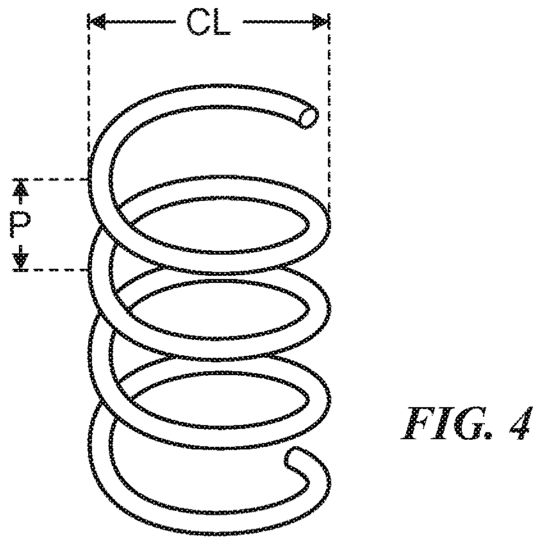

The treatment device may instead be configured to bore the hole by sequentially applying a plurality of laser pulses in a predetermined location pattern that may be repeated for multiple layers of pulses until the desired depth D is reached. Each pulse in a layer may at least partially overlap in location with at least one other pulse in the same layer. An example is shown in FIGS. 3 and 4. Each spot 202*a-f* represents the location of a pulse in a single layer of pulses applied to a treatment area on the skin. Five of the spots 202*b-f* in the example of FIG. 3 are arranged in a circular pattern. However, depending on the shape of the desired hole, the spots 202*b-f* may be arranged in a different configuration, and more or fewer spots 202*b-f* may be used depending on the desired cross-sectional size of the hole. Another spot 202*a* is located at the center of the pattern and overlaps with each of the five outer spots 202*b-f* forming the circular pattern. Depending on the diameter of the hole, the central spot 202*a* may be disregarded if the other spots 202*b-f* overlap with one another at the center of the pattern. In other embodiments, multiple circles of spots may be necessary if a larger diameter circular hole is desired. In other words, the cross-sectional size and shape of the desired hole may dictate the number and arrangement of spots in a layer. In the example of FIG. 3, the treatment device may apply the laser at the central spot 202*a* and then proceed to each of the outer spots 202*b-f* in a counterclockwise or clockwise direction. The treatment device may use the scanner servo controller 27 to operate scanner motors or similar components of the laser applicator 16 or the like to move the spot location automatically during operation.

FIG. 3 shows a circle formed by a line crossing the center of each of the five outer spots 202*b-f*. For a hole having a diameter d between about 360 microns to about 400 microns (delineated by circles $S_{min}$ and $S_{max}$), and with a beam size of about 170 microns, the center line circle may have a diameter CL of about between about 240 microns to about 280 microns. Different beam sizes and hole diameters may result in different dimensions for the center line circle.

If necessary, multiple layers of the pattern may be applied at the treatment area, with each successive layer resulting in deepening of the hole. The number of layers required to reach the desired depth D may depend on the ablation depth of the pulses. The ablation depth for the pulses may be in a range of between about 1 micron to about 100 microns, and more particularly, between about 25 microns and about 50 microns. In the example embodiment, the ablation depth for the pulses is about 36 microns, which is a compromise between drilling speed and minimizing thermal damage. To achieve this ablation depth, each pulse may have a fluence of about 9.25 J/cm$^2$, which with a pulse diameter of about 170 microns results in an energy delivery of about 2.1 mJ per pulse. With an ablation depth of about 36 microns, it may take approximately 27 layers to reach a depth D of approximately 1.0 mm. As a result, it may take 162 individual pulses to drill a ~1.0 mm deep, 360-400 nm diameter hole, using a total energy delivery of about 340.2 mJ. Each pulse duration may be about 250 microseconds, although other pulse durations may be used depending on the desired effects, laser frequency, and the like. Similarly, the time between pulses may be about 100 microseconds, but can be varied from between about 50 to about 200 microseconds. In addition, in some embodiments, the system may add a longer delay of between about 200 to about 400 microseconds between layers of the pattern, with 200 microseconds as a preferred embodiment. Referring to FIG. 4, three-dimensionally, the center lines formed by the outer spots 202*b-f* in each layer may form a spiral pattern with the diameter CL and having a pitch p approximately equal to the pulse ablation depth, e.g., 36 microns in the example given above.

The ratio of the delivered energy between ablation and thermal injury is believed to have an impact on the results achieved through use of embodiments covered under this disclosure. Without being bound by any particular theory, the mechanisms of ablation and thermal injury created by the laser beam are different. It is desirable to obtain a favorable balance between tissue ablation and thermal injury. Taking the $CO_2$ laser ratio of 40:60 described above, this process leaves behind necrotic tissue at the drill site, which is believed to unnecessarily drag out the healing period. Rather, it is more beneficial that the heat-effected tissue result in collagen shrinkage without local necrosis. In particular, it is believed that with a proper level of thermal injury, immediate contraction of the hole may be stimulated and cause new collagen to be produced over a shorter timespan than with other methods. This may lead to faster healing and faster visibility of results based on the increased timing in skin tightening. Accordingly, the delivered ratio of ablative to thermal injury may be between about 95:5 and about 50:50, more preferably between about 95:5 and 65:35, and even more preferably between about 85:15 and about 75:25. For example, with the fluence described above and using the treatment device shown in FIG. 1, the delivered energy for the laser coring example is close to 20% (2/9.25=~ 21.6%) for thermal injury (e.g., ratio of around 80:20).

The treatment device may be used to form patterns of holes on face and/or neck skin tissue of the patient. In addition to a single hole, various patterns of spaced-apart holes may include a line, a rectangle, a square, or other patterns. The scanner servo controller 27 may drive the scanner motors in the laser applicator 16 or like equipment to move the beam to the appropriate location for each hole in the pattern of holes. Hole patterns may also vary in size. For example, a square may be 5 mm×5 mm or 10 mm×10 mm or 15 mm×15 mm or the like. Various sizes of shapes may be utilized in keeping within the spirit and scope of the invention. A user may be enabled to select a particular pattern from a plurality of options, as will be described in further detail below. The use of a particular shape may depend on the particular needs of the patient and result to be accomplished. For example, a line pattern may be used primarily for treating scars, while rectangular or square patterns may be more useful for lifting/tightening procedures.

The hole patterns may also vary by hole density, which can be designated by metrics such as the number of holes per unit area, a percentage of the area consumed by holes, combinations thereof, or the like. In one example embodiment, the treatment device may enable a user to select from a list of predetermined pattern densities ranging from about 1% to about 10% coverage. The table below lists the example spacing between holes in the hole pattern based on the selected density. These numbers can also vary in other embodiments, depending on the hole diameter, desired effects, and/or other variables.

| % Coverage | Distance between holes |
|---|---|
| 1% | 3.190 mm |
| 2% | 2.255 mm |
| 3% | 1.842 mm |
| 4% | 1.595 mm |
| 5% | 1.426 mm |
| 6% | 1.302 mm |
| 7% | 1.205 mm |
| 8% | 1.127 mm |
| 9% | 1.063 mm |
| 10% | 1.008 mm |

Figure 5:
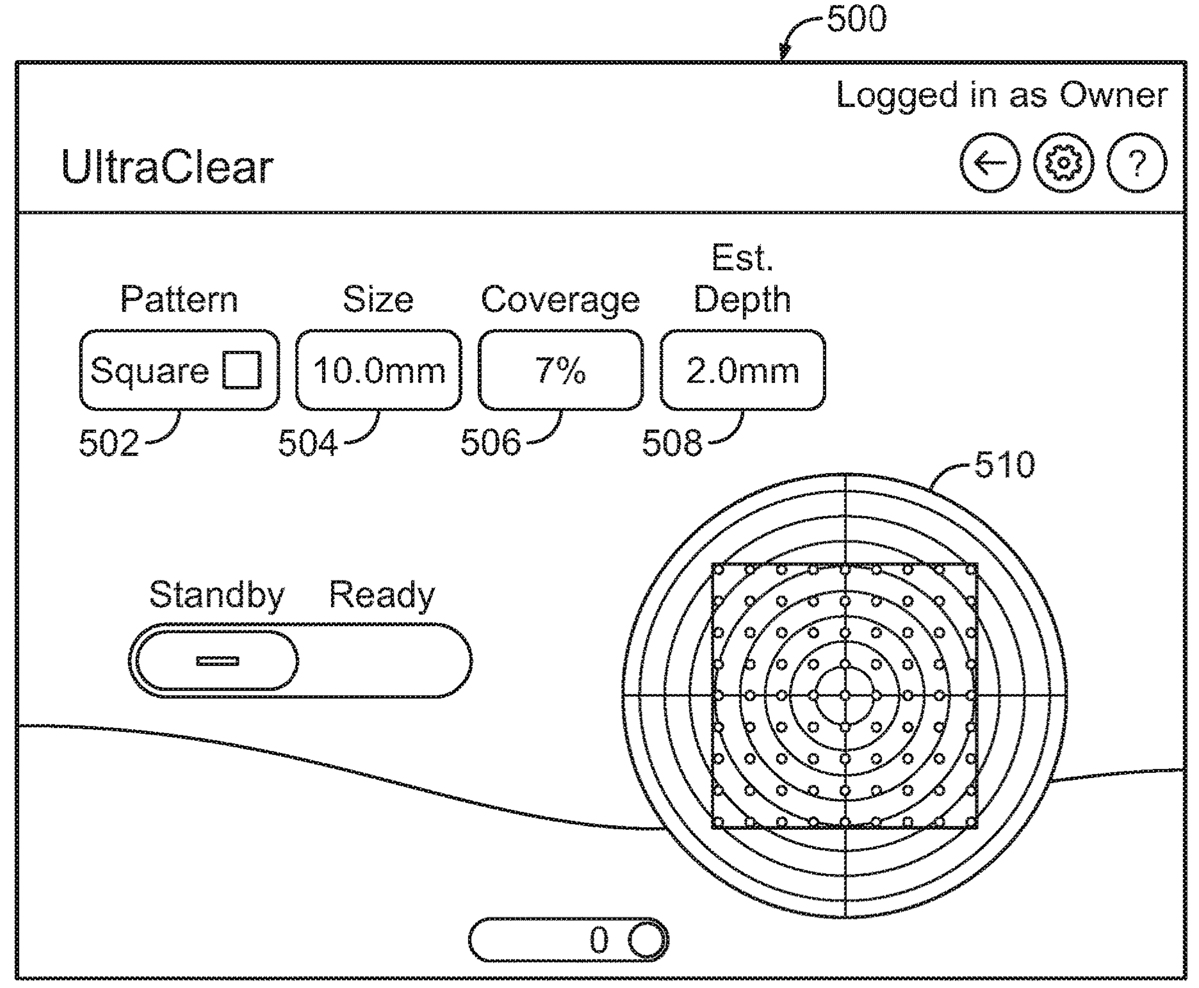
FIG. 5 is an example user interface for selecting various parameters for a laser coring operation in accordance with an example embodiment of the present invention.

FIG. 5 is an example user interface screen 500 which may be displayed on the touch panel 10 or other internal or external display of the treatment device 24 for selecting various options for a laser coring operation, particularly with respect to the hole pattern and hole depth. For example, the user interface 500 provides four selection buttons 502, 504, 506, 508, each of which may provide a drop-down menu upon selection. However, other configurations for variable selection may be used as well. In the example of FIG. 5, a pattern selection button 502 may enable the user to select the hole pattern shape (e.g., square, rectangle, line, single hole, or the like). A size selection button 504 may allow the user to specify the size of the selected hole pattern. In the example shown, only the size of the maximum dimension is displayed (e.g., the long side of a rectangle or the like). However, other methods of displaying selected or selectable hole pattern sizes may be used as well, including displaying multiple measurements (e.g., length and width) for two-dimensional shapes, overall area, circumference or perimeter, combinations thereof, or the like. A coverage button 506 may allow the user to specify the hole density. In this example, the user is provided the opportunity to select a percent coverage between 1% and 10% in intervals of 1%. However, other options and ranges for selecting density may be used as well. An estimated depth button 508 may enable the user to select the depth D of the hole. In this example, the user may select between 0.5 and 4.0 mm in intervals of 0.5 mm. A preview window 510 may be provided to visualize some or all of the selections. In the example of FIG. 5, the preview window 510 visually represents the selected square hole pattern of size 10.0 mm at 7% coverage.

In some embodiments, one or all of the hole pattern shape, hole pattern size, coverage, and hole depth may be predetermined or preset in the controller 22 or may be determined in response to selection of other variables or as part of a selectable "package". In some embodiments, additional variables for selection by the user may include one or more of pulse energy, fluence, hole diameter, pulse ablation depth, number of pulses, pulse spacing, pulse duration, spot size, or the like.

Figure 6:
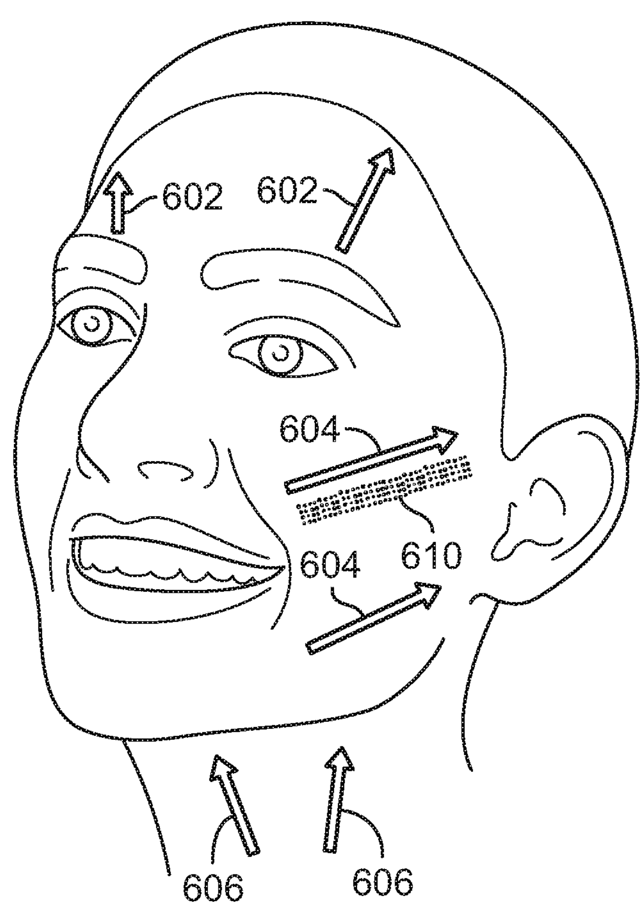
FIG. 6 is a schematic diagram illustrating example lifting vectors on the human face and the relation of laser coring operations with respect thereto in accordance with an example embodiment of the present invention.

Laser coring operations according to embodiments described herein are particularly useful for performing vector tightening or lifting procedures on patients. Using lifting vectors may be preferable to total facial area treatments in some circumstances, particularly as safety is increased, treatment time is decreased, the treatment can be tailored, and there is a more predictable and tolerable downtime. Vector tightening or lifting involves treating certain areas of the skin to create lifting forces in particular directions leading to improved appearance, because as humans age, gravitational forces pull the skin down to form wrinkles and a sagging appearance to the skin. FIG. 6 shows an example of some beneficial vector patterns. For example, arrows 602 show vectors for the forehead extending generally from the eyebrows to the hair line. Arrows 604 show vectors for the cheeks which extend in a direction toward the ear. Arrows 606 show vectors for the neck that extend generally vertically toward the patient's jawline. Although not shown, other vectors are known as well, such as in the area between the nose and the mouth.

Laser coring operations may be used to perform vector tightening or lifting by, for example, applying one or more of the hole patterns described above in particular locations of the face and extending parallel to the desired vector(s). In an example shown in FIG. 6, a square pattern 610 is used and repeated to form a stripe extending generally in the direction of a vector on the patient's cheek. The treatment device, or appropriate components thereof, may be moved relative to the patient, either automatically or by manual control, for placing each hole pattern to form the stripe. Multiple stripes may be formed as needed in appropriate locations. It is believed that through the thermal effects from the laser coring and the placement of the patterns, the healing of the skin produces forces in the direction of the indicated vector (s) so as to tighten and effect aesthetic enhancement.

In testing, vector treatments with the laser coring operations described above have produced permanent skin tightening with faster results, lower pain, and shorter downtime. The treatment itself can be performed in less than 30 minutes and using only topical anesthetics. Patients experience minimal bleeding and lower pain during and after the procedure. Patients also have been able to resume normal activities in less than 100 hours after the procedure. Skin tightening effects have also been observed almost immediately. The procedure is also safe for all skin types and can be performed on any area in the face or body, as compared to, for example, mechanical micro-coring.

Those skilled in the art will recognize that boundaries between the above-described operations are merely illustrative. The multiple operations may be combined into a single operation, a single operation may be distributed in additional operations and operations may be executed at least partially overlapping in time. Further, alternative embodiments may include multiple instances of a particular operation, and the order of operations may be altered in various other embodiments.

While specific and distinct embodiments have been shown in the drawings, various individual elements or combinations of elements from the different embodiments may be combined with one another while in keeping with the spirit and scope of the invention. Thus, an individual feature described herein only with respect to one embodiment should not be construed as being incompatible with other embodiments described herein or otherwise encompassed by the invention.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined herein.

We claim:

1. A laser treatment device comprising:

a laser source configured to emit optical energy at a laser wavelength between about 2,700 nm and about 3,500 nm;

a laser applicator configured to receive the optical energy emitted by the laser source and deliver the received optical energy to a target area of human tissue; and a controller configured to control the laser source and laser applicator to form a hole in the human tissue within the target area by delivering a plurality of laser pulses to a plurality of locations forming a pattern within the target area, each of the plurality of locations in the pattern partially overlapping with at least one other of the plurality of locations in the pattern, the pattern having a center and wherein:

i. at least a portion of the plurality of locations partially overlap with the center of the pattern, or ii. one of the plurality of locations is located at the center of the pattern and partially overlaps with at least one other of the plurality of locations, the controller being configured to provide each of the plurality of pulses with a fluence above an ablation threshold fluence for the laser wavelength such that a thermal injury percentage for energy delivered by each pulse is between about 5% and about 50%, the thermal injury percentage being determined by dividing the ablation threshold fluence for the laser wavelength by the fluence of each pulse.

2. The laser treatment device of claim 1, wherein the controller is further configured to control the laser source and laser applicator to form a plurality of holes, spaced apart from one another, within the target area.

3. The laser treatment device of claim 2, wherein the controller is configured to control the laser source and laser applicator to space the plurality of holes apart from one another by a distance of between about 1.000 mm and 4.000 mm in the target area.

4. The laser treatment device of claim 3, wherein the controller is configured to receive a selection from a user for the distance between the plurality of holes.

5. The laser treatment device of claim 2, wherein the controller is configured to one of (i) store a predetermined pattern for arranging the plurality of holes in the target area, or (2) receive a selection from a user of a pattern for arranging the plurality of holes in the target area.

6. The laser treatment device of claim 1, wherein the thermal injury percentage for energy delivered by each pulse is between about 5% and about 35%.

7. The laser treatment device of claim 6, wherein the thermal injury percentage for energy delivered by each pulse is between about 15% and about 25%.

8. The laser treatment device of claim 1, wherein the controller is configured to control the laser source and the laser applicator such that at least a portion of the plurality of locations together form a ring.

9. The laser treatment device of claim 8, wherein the controller is configured to control the laser source and the laser applicator such that one of the plurality of locations is located at a center of the ring.

10. The laser treatment device of claim 1, wherein the controller is configured to continue delivering laser pulses to the target area in the pattern until a set depth of the hole is obtained.

11. The laser treatment device of claim 10, wherein the set depth of the hole is between about 0.5 mm and about 4.0 mm.

12. The laser treatment device of claim 1, further comprising a user interface in communication with the controller, wherein the controller is configured to receive, via the user interface, a user selection of one or more of a hole pattern for arranging a plurality of holes to be formed by the laser treatment device, a size of the hole pattern, spacing of the plurality of holes within the hole pattern, or a hole depth.

13. The laser treatment device of claim 1, wherein the controller is configured to form the hole having a diameter of between about 250 microns and about 400 microns.

14. The laser treatment device of claim 1, wherein the controller is configured to set the fluence for each pulse such that an ablation depth of each pulse is between about 25 microns and about 50 microns.

15. A method of forming a hole in a target area of human tissue using a laser treatment device having a laser source configured to emit optical energy at a laser wavelength between about 2,700 nm and about 3,500 nm, a laser applicator configured to receive the optical energy emitted by the laser source and deliver the received optical energy to the target area, and a controller the method comprising:

(a) delivering, by the laser source and the laser applicator, a laser pulse having a set fluence to the target area;

(b) changing, by the controller, location in the target area and delivering, by the laser source and the laser applicator, a laser pulse having the set fluence;

(c) repeating step (b) to form a pattern including a plurality of locations, each of which partially overlaps with at least one other of the plurality of locations in the pattern, the pattern having a center and wherein:

i. at least a portion of the plurality of locations partially overlap with the center of the pattern, or ii. one of the plurality of locations is located at the center of the pattern and partially overlaps with at least one other of the plurality of locations, the set fluence for each of the laser pulses being above an ablation threshold fluence for the laser wavelength such that a thermal injury percentage for energy delivered by each pulse is between about 5% and about 50%, the thermal injury percentage being determined by dividing the ablation threshold fluence for the laser wavelength by the fluence of each pulse.

16. The method of claim 15, wherein the thermal injury percentage for energy delivered by each pulse is between about 5% and about 35%.

17. The method of claim 16, wherein the thermal injury percentage for energy delivered by each pulse is between about 15% and about 25%.

18. The method of claim 15, further comprising repeating delivery of laser pulses in the pattern until a set depth of the hole is obtained.

19. The method of claim 18, wherein the set depth of the hole is between about 0.5 mm and about 4.0 mm.

20. A method of treating human tissue, the method comprising:

forming a plurality of holes in a target area according to the method of claim 15.

* * * * *